(12) United States Patent
Lokey et al.

(10) Patent No.: US 7,964,702 B2
(45) Date of Patent: Jun. 21, 2011

(54) PHALLOIDIN DERIVATIVES AND METHODS FOR THEIR SYNTHESIS

(75) Inventors: R. Scott Lokey, Santa Cruz, CA (US); Laura A. Schuresko, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1000 days.

(21) Appl. No.: 11/800,100

(22) Filed: May 4, 2007

(65) Prior Publication Data

US 2007/0275886 A1 Nov. 29, 2007

Related U.S. Application Data

(60) Provisional application No. 60/798,137, filed on May 4, 2006.

(51) Int. Cl.
*A61K 38/12* (2006.01)

(52) U.S. Cl. ....................................................... 530/334
(58) Field of Classification Search ........................ None
See application file for complete search history.

(56) References Cited

OTHER PUBLICATIONS

Anderson et al (J Org Chem 'A solid-phase approach to the phallotoxins: total synthesis of [Ala7]-phalloidin' (2005) 70, pp. 4578-4584).*
Zanotti et al (Chem Eur J 'Solid state and solution conformation of [Ala7]-phalloidin: a synthetic phallotoxin analogue' (2001) 7 No. 7 pp. 1479-1485).*
Anonymous, *Peptide Synthesis*, Wikipedia online free encyclopedia, http://en.wikipedia.org/wiki/Peptide_synthesis, dated Jan. 5, 2011; downloaded and printed Jan. 6, 2011.
Anonymous, *Tetrakis(triphenylphosphine)palladium*, Chemical Book webpage, http://www.chemical book.com/Chemical/ProductProperty_EN_CB6163934.htm downloaded and printed Oct. 14, 2010.
Anonymous, *Dichloromethane*, Wikipedia online free encyclopedia, http://en.wikipedia.org/wiki/Dichloromethane, dated Jan. 6, 2011; downloaded and printed Jan. 6, 2011.
Anonymous, *Non-nucleophilic base*, Wikipedia online free encyclopedia, http://en.wikipedia.org/wiki/Non-nucleophilic_base, dated Apr. 7, 2010; downloaded and printed Oct. 14, 2010.

* cited by examiner

*Primary Examiner* — Cecilia Tsang
*Assistant Examiner* — Ronald T Niebauer
(74) *Attorney, Agent, or Firm* — Matthew Kaser; Adam Warwick Bell

(57) ABSTRACT

The invention provides a cyclomonomer having actin-binding activity. The cyclomonomer is of utility for the study of the molecular biology of actin polymerization. The cyclomonomer is also useful for the study of and treatment of the toxic effects of *Amanita* sp. poisoning.

5 Claims, 5 Drawing Sheets phalloidin (1)   Glu⁷-phalloidin (2)

| Sequence | thioether product | : | disulfide product | |
|---|---|---|---|---|
| Fmoc-NH-Cys-Pro-Ala-Trp-OH | 2 | : | 1 | SEQ ID NO:3 |
| Fmoc-NH-Cys-Hyp(OTIPS)-Ala-Trp-OH | 6.6 | : | 1 | SEQ ID NO:14 |

Scheme 1. Testing solid phase $I_2$-mediated cyclization strategy using tetrapeptide model systems.

Chlorotritylchlorohydride resin

Acid-sensitive sidechain protection groups and linker 1 phalloidin
2 glu⁷-phalloidin

PHALLOIDIN DERIVATIVES AND METHODS FOR THEIR SYNTHESIS

This application claims the benefit of U.S. Provisional Patent Application Ser. No. 60/798,137, filed May 4, 2006, which is herein incorporated by reference in its entirety.

This invention was made partly using funds from the National Institutes of Health contract number 1RO1 CA104569-01 and -03. The U.S. Federal Government may have certain rights to this invention.

TECHNICAL FIELD

The present invention provides novel compounds having filamentous actin binding activity. The invention further provides methods for synthesizing the compounds.

BACKGROUND ART

Phalloidin is an actin-binding toxin whose chemistry and bioactivity have been studied since the early 1900s (see, for example, Wieland, T., (1986) Peptides of Poisonous Amanita Mushrooms. ed.; Springer-Verlag: New York, page 256). Phalloidin binds with high affinity to filamentous actin (F-actin) and lowers the critical concentration of actin polymerization in solution. It has been used extensively to study actin dynamics in vitro, and fluorescent analogs of phalloidin provide highly specific reagents for microscopic visualization of the actin cytoskeleton (see, for example, Pringle, J. R., et al. (1991) Methods Enzymol. 194: 729-731. The natural source of phalloidin, *Amanita phalloides*, the Death Cap mushroom, lives in a complex ecological relationship with host trees and is widely considered to be uncultivable (Wieland (1986) supra). Pure phalloidin sells for ~$150 per milligram and its fluorescent conjugates are much more expensive. In our efforts to develop high-throughput cell-based screens for compounds that modulate actin cytoskeletal morphology, we have sought an inexpensive source of fluorescently labeled phalloidin. Although there have been a number of syntheses of phalloidin analogs both in solution and on the solid phase, no synthetic route has been published with yields significant enough to provide this reagent in practical quantities. These syntheses reported yields ranging from 0.5% to 1.3% and relied on the preparation of relatively complex building blocks in solution. (See Wulf, E. et al. (1979) Proc. Natl. Acad. Sci., 76: 4498-4502; Falcigno, L. et al. (2001) Chemistry—A European Journal, 7: 4665-4673; Zanotti, G. et al. (2001) Chem. Eur. J. 7: 1479-1485; and Anderson, M. O. and Guy, R. K., (2005) J. Org. Chem. 70: 4578-4584.)

Phalloidin is a bicyclic heptapeptide that contains an unusual bridging thioether linkage between the Cys and Trp residues. The natural product contains four common L-amino acids, a D-threonine residue, an unusual γ,δ-dihydroxy-L-leucine residue, and the rare cis epimer of 3-hydroxy-L-proline. Structure-activity studies have shown that the γ,δ-dihydroxy-L-leucine side chain is not essential for actin binding (see Anderson, M. O. and Guy, R. K., (2005) supra; and Wieland, T., (1983) Int. J. Pept. Protein Res., 22: 257-276).

In efforts to develop high-throughput cell-based screens for compounds that modulate actin cytoskeletal morphology, an inexpensive source of fluorescently labeled phalloidin has been sought.

It is desirable to provide improved approaches, including both compounds and methods for their synthesis, for use in the study of the cytoskeleton and cellular morphology and for developing compounds for treating patients suffering from liver failure due to consumption or ingestion of phalloidin and related compounds.

SUMMARY OF THE INVENTION

The invention provides a novel compound having filamentous actin binding activity. The invention further provides a method for synthesizing the compound.

In one embodiment the invention provides a cyclomonomer having actin binding activity, the cyclomonomer comprising a heptapeptide having a cystyl residue, a prolyl residue, and a tryptophanyl residue and wherein the cystyl residue and the tryptophanyl residue are linked by a thioether bond. In a preferred embodiment the actin is filamentous actin. In another preferred embodiment the heptapeptide further comprises an amino acid residue selected from the group consisting of an alanyl residue, a leucyl residue, a glycyl residue, a threonyl residue, and a glutamyl residue. In a more preferred embodiment the amino acid residues are L-isomers. In another more preferred embodiment the amino acid residues are D-isomers. In another preferred embodiment the prolyl residue is a hydroxyprolyl residue. In a yet more preferred embodiment the prolyl residue is a protected cis-4-hydroxy-L-prolyl residue, the protection comprising a triisopropylsilyl moiety. In a most preferred embodiment the cyclomonomer is bicyclo(Ala1-D-Thr2-Cys3-cis-4-hydroxy-Pro4-Ala5-2-mercapto-Trp6-Glu7)(S-3→6).

In one embodiment, a side chain of the cyclomonomer is selected from the group consisting of hydrogen, fluoride, cyano, halogen, carboxylic acid, a salt of carboxylic acid, sulfonic acid, $C_1$-$C_6$ alkyl, $C_1$-$C_6$ alkoxy, aryl, heteroaryl, -L-$R_X$ and -L-$S_C$, wherein said alkyl or alkoxy is optionally substituted by carboxylic acid, sulfonic acid, or halogen and said aryl or heteroaryl is optionally substituted one or more times by $C_1$-$C_6$ alkyl, $C_1$-$C_6$ perfluoroalkyl, cyano, halogen, azido, carboxylic acid, sulfonic acid, or halomethyl, a carboxylic acid ester of a $C_1$-$C_6$ alcohol, a $C_1$-$C_6$ alkyl that is optionally substituted one or more times by carboxylic acid, sulfonic acid, amino, or halogen, nitro, hydroxy, azido, amino, hydrazino, -L-$R_X$ and -L-$S_C$, $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, $R_x$ is a reactive group; and $S_C$ is a conjugated substance.

In another embodiment the heptapeptide comprises amino acid residues selected from the group consisting of the naturally occurring amino acids and synthetic derivatives thereof.

The invention also provides a method for synthesizing a cyclomonomer having actin binding activity, the method comprising the steps of (i) providing glutamate, Fmoc, allyl ester, 2-chlorotrityl polystyrene resin, tryptophan, α-protected alanine, α-protected cis-4-hydroxy-proline, α-protected cysteine, α-protected D-threonine, (ii) α-protecting the N-terminus of glutamate using base-labile Fmoc, (iii) protecting the C-terminal of the Fmoc-protected glutamate using allyl ester to create a modified glutamate, (iv) linking the side chain of the modified glutamate to 2-chlorotrityl polystyrene resin, (v) linking the N-terminus of the modified glutamate to tryptophan using standard Fmoc chemistry thereby creating a dipeptide, (vi) elongating the dipeptide with N-α-protected alanine using standard Fmoc chemistry thereby creating a tripeptide, (vii) elongating the tripeptide with N-α-protected cis-4-hydroxy-proline using standard Fmoc chemistry thereby creating a tetrapeptide, (viii) elongating the tetrapeptide with N-α-protected, S-trityl protected cysteine using standard Fmoc chemistry thereby creating a pentapeptide, (ix) elongating the pentapeptide with N-α-protected D-threonine using standard Fmoc chemistry thereby creating a hexapeptide, (x) elongating the hexapeptide with N-α-protected alanine using standard Fmoc chemistry thereby creating a heptapeptide, (xi) removing the N-terminal Fmoc and the C-terminal allyl ester, (xii) deprotecting the heptapeptide using $Pd(PPh_3)_4$, NMM, acetic acid, DCM, 20% piperidine, and DMF thereby creating a modified heptapeptide, (xiii) cyclizing the modified heptapeptide using diphenylphosphorylazide (DPPA), DIPEA, and DMF thereby creating a cyclomonomer, (xiv) treating the cyclomonomer with $I_2$ in DMF thereby creating a thioether bond between the cysteine residue and the tryptophan residue, (xv) cleaving the modified cyclomonomer from the resin using 1% TFA in $CH_2Cl_2$, the steps resulting in the synthesis of bicyclo(Ala1-D-Thr2-Cys3-cis-4-hydroxy-Pro4-Ala5-2-mercapto-Trp6-Glu7)(S-3→6).

In an alternative embodiment the method further comprises the step of elongating the tripeptide using side chain-protected cis-4-hydroxy-proline.

In another alternative embodiment the method further comprises the step of elongating the pentapeptide using side chain-protected D-threonine.

In yet another alternative embodiment the method further comprises the step of treating the modified cyclomonomer using 50% TFA in $CH_2Cl_2$.

In a still further alternative embodiment the method further comprises the step of treating the modified cyclomonomer using 50% HF in THF.

The invention also provides a method for treating a subject having the symptoms of hepato-toxicity due to ingestion of *Amanita* sp., the method comprising the step of providing the subject with a pharmaceutical composition comprising the cyclomonomer disclosed herein and a pharmaceutical carrier in a sufficient amount to reduce and alleviate the symptoms.

DETAILED DESCRIPTION OF THE INVENTION

The invention disclosed herein provides phalloidin and derivatives thereof that can be used to study the effects of fungal and synthetic toxins on the cellular cytoskeleton, in particular upon actin polymerization, such as during cell division, cell proliferation, cellular and tissue differentiation, and metabolic and dynamic processes in tissue, such as those of muscle, nerve, endothelium, the blood circulatory system, and the lymphatic system.

As used herein and in the appended claims, the singular forms "a," "an," and "the" include plural reference unless the context clearly dictates otherwise. Thus, for example, a reference to "an amino acid residue" includes a plurality of such amino acid residues, and a reference to "a side chain" is a reference to one or more side chains and equivalents thereof, and so forth.

The naturally occurring amino acids include, but are not limited to, alanine, asparagine, aspartic acid or aspartate, cysteine, cystine, glutamine, glutamic acid or glutamate, phanylalanine, glycine, histidine, isoleucine, lysince, leucine, methionine, proline, arginine, serine, threonine, valine, tryptophan, tyrosine, and derivatives thereof. The amino acid can be an L-isomer or can be a D-isomer. The side chains of the amino acid residues can be modified, for example, by phosphorylation, sulphation, or acetylation.

In efforts to develop high-throughput cell-based screens for compounds that modulate actin cytoskeletal morphology, an inexpensive source of fluorescently labeled phalloidin has been sought.

Figure 1:
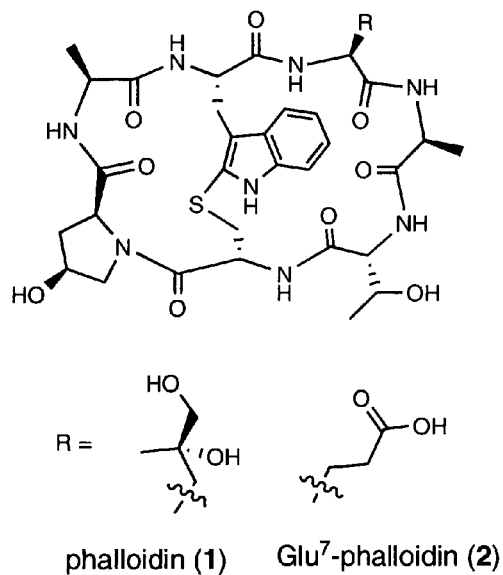
FIG. 1 illustrates the chemical structures of phalloidin (1) and Glu7-phalloidin (2).

Herein we report a solid-phase synthesis of $Glu^7$-phalloidin (FIG. 1; 2) in 50% overall yield from simple starting materials. Derivatization of the $Glu^7$ side chain yielded a fluorescent analog that stains F-actin in fixed cells at a concentration comparable to commercial phalloidin-based probes. The phalloidin derivative can be a tetrapeptide, a pentapaptide, a hexapeptide or a heptapeptide.

Figure 2:
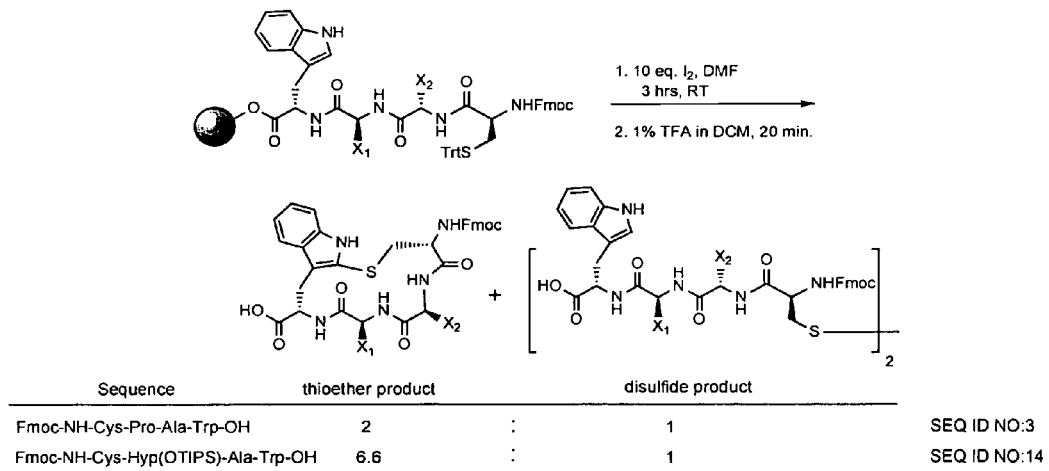
FIG. 2 illustrates a process for testing solid phase $I_2$-mediated cyclization strategy using tetrapeptide model systems (scheme 1).

The natural product found in the mushroom contains four common L-amino acids, a D-threonine residue, an unusual γ,δ-dihydroxy-L-leucine residue, and the rare cis epimer of 4-hydroxy-L-proline. Since the γ,δ-dihydroxyleucine side chain is not essential for actin binding (see, for example, Falcigno, L. et al. (2001) supra) we replaced this residue with glutamic acid. This substitution provided both a handle for linking to the solid phase and a site for fluorophore attachment (FIG. 2; 2, Scheme 1). The cis-4-hydroxyproline residue was prepared according to published methods and the remaining amino acids were commercially available (see, for example, Anderson, M. O. and Guy, R. K., (2005) supra; Weir, C. A. and Taylor, C. M. (1999) J. Org. Chem., 64: 1554-1558; and Weir, C. A. and Taylor, C. M. (1999) Org. Lett., 1: 787-789).

The approach herein to form the thioether bridge was inspired by a side reaction reported during $I_2$-mediated deprotection of S-tritylcysteine (Cys[Trt]) in peptides containing tryptophan. (Alternatively, thionation may occur by iodination of the indole to form a 3-iodoindolenine intermediate, which undergoes nucleophilic attack on C2 by the sulfur atom followed by dehydrohalogenation.) The minor product was attributed to thioether formation between the Cys and Trp residues, which occurred presumably via attack of the tryptophan indole by a highly electrophilic sulfenyl iodide species (see Sieber, P. et al. (1980) Helvet. Chim. Acta, 63: 2358-2363). Using model peptides based on the sequence Cys(Trityl)-Gly$_n$-Trp, Sieber et al. (1980, supra) showed that I$_2$ treatment led to efficient thioether formation that out-competed disulfide dimerization when n>3.

When similar conditions were applied to the solid-phase synthesis of model peptides based on the thioether-containing sequence of phalloidin, the only observed products were the desired thioether and the dimer resulting from on-resin intermolecular disulfide formation. Using the sequence H$_2$N-Cys-Pro-Ala-Trp-OH (SEQ ID NO: 1), at a loading value of 0.1 mmol/g, cyclization out-competed dimerization by a 2:1 ratio (FIG. 2; Scheme 1). When the L-proline residue was replaced with triisopropylsilyl (TIPS)-protected cis-4-hydroxy-L-proline, the ratio of thioether to disulfide increased to 6.6:1. These results pointed toward a solid-phase synthesis of Glu$^7$-phalloidin using an I$_2$-mediated cyclization strategy for the thioether bridge-forming step.

Figure 3:
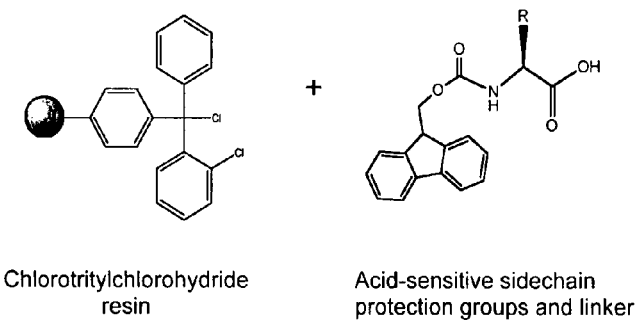
FIG. 3 illustrates the solid phase peptide synthesis (SPPS) strategy showing the chlorotritylchloride resin and the Fmoc protection groups and linker.
Figure 4:
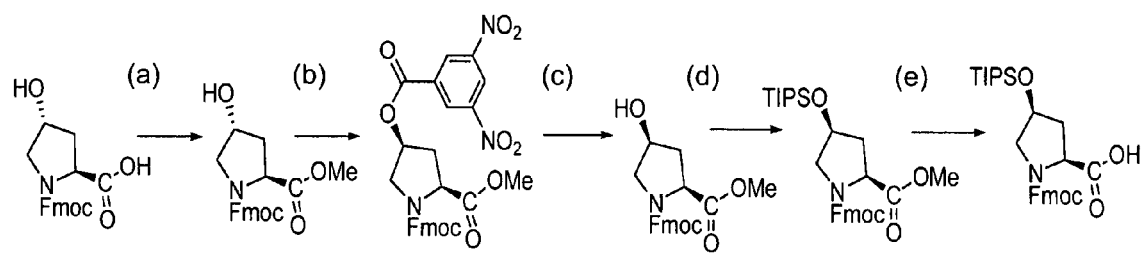
FIG. 4 illustrates the synthesis of Fmoc-cis-Hyp(OTIPS)-OH including the reagents (a) $Cs_2CO_3$, MeI; (b) $PPh_3$, DIAD, 3,5-dinitrobenzoic acid; (c) $NaN_3$, 15-crown-5; (d) TIPS-Cl, imidazole; and (e) LiOH, $H_2O$.
Figure 5:
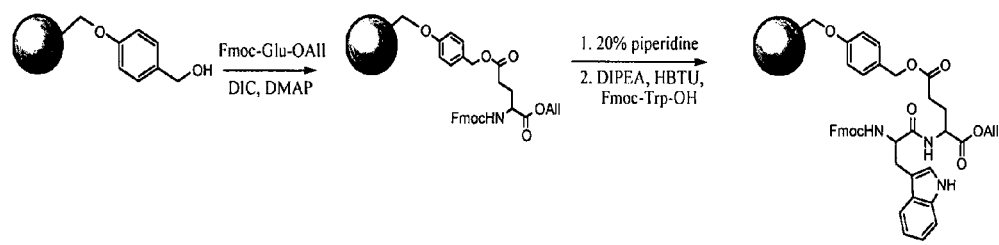
FIG. 5 illustrates a standard peptide coupling reaction to synthesize the final linear sequence Fmoc-Ala-d-Thr(TBU)-Cys(trt)-Hyp(OAc)-Ala-Trp-Glu(OAll).

To generate the appropriate peptide precursor, the Glu$^7$ residue was C-terminally protected as an allyl ester and linked through its side chain to 2-chlorotrityl polystyrene resin (see FIG. 3). The heptapeptide was elongated using standard Fmoc chemistry (FIG. 5; Scheme 2), and after removal of the N-terminal Fmoc and C-terminal allyl ester, the peptide backbone was cyclized using diphenylphosphorylazide (DPPA). Cleavage from the resin and high pressure liquid chromatography-mass spectroscopy (HPLC-MS) analysis showed that the macrolactamization proceeded efficiently. No cyclodimer or higher oligomers were observed.

It should be noted that initial attempts to remove the final Fmoc group using 20% piperidine in dimethylfluoride (DMF) resulted in the formation of unidentified side-products and a low overall yield of Glu$^7$-phalloidin. Treatment of the linear peptide with 1% diazabicycloundecane (DBU) in DMF, however, afforded clean deprotection of the N-terminus and led to a dramatic increase in yield of the final product.

Figure 6:
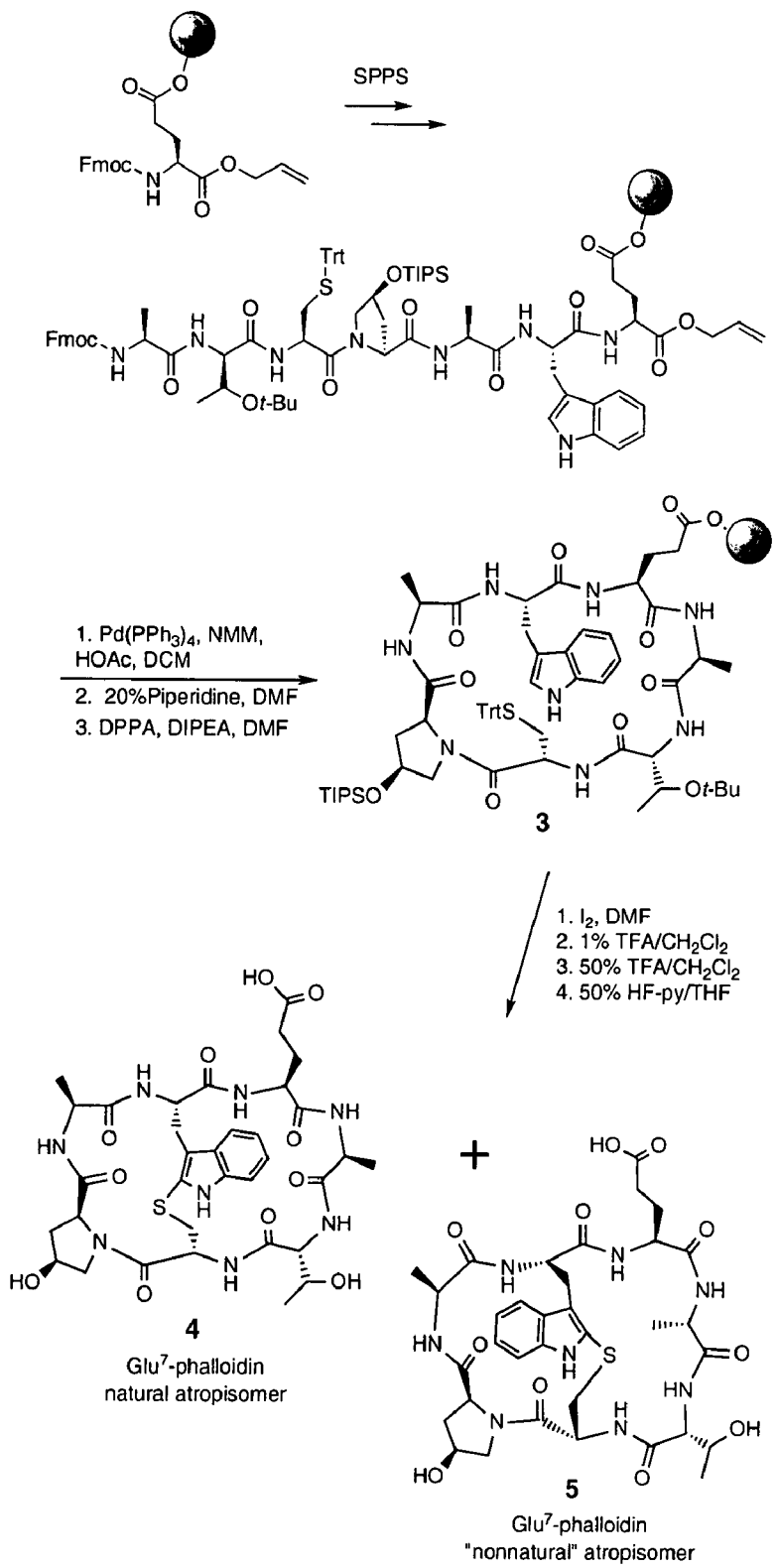
FIG. 6 illustrates a process for SPPS of $Glu^7$-phalloidin (scheme 2).

When resin-bound cyclic peptide 4 was treated with I$_2$ in DMF, we observed complete conversion to thioether with no intermolecular disulfide dimer detected (FIG. 6; Scheme 2). Cleavage from the resin was performed with 1% trifluoroacetic acid (TFA)/CH$_2$Cl$_2$, followed by removal of the D-Thr and 3-hydroxyproline side chain protecting groups using 1:1 TFA/CH$_2$Cl$_2$ and then 50% HF-pyridine/THF. HPLC purification yielded two isomeric compounds in a 1:1 ratio whose circular dichroism (CD) and $^1$H NMR spectra were consistent with the natural (2) and "unnatural" (5) atropisomers of phalloidin. The overall yield of the purified material was 50% based on the initial resin loading.

It is noted that synthetic phallotoxins can exist as two isolatable atropisomers. The synthetic route reported here accesses the natural atropisomer exclusively, as determined by comparison of the CD spectrum of Glu$^7$-phalloidin to that of the authentic natural product. In addition, the distinctive upfield chemical shift of the Ala$^5$ methyl group is diagnostic of the natural atropisomer, due to its proximity to the anisotropy field of the tryptophan indole ring (see Anderson, M. O. et al., (2005) J. Org. Chem. 70: 4578-4584).

The ability to select atropisomers in bridged cyclic structures by changing the order of cyclization has been exploited in syntheses of the natural product vancomycin (see, for example, Boger, D. L. et al. (2001) J. Am. Chem. Soc. 123: 1862-1871; Boger, D. L. et al. (1999) J. Am. Chem. Soc. 121: 10004-10011; Nicolaou, K. C. et al. (1999) Chemistry—A European Journal, 5: 2622-2647; and Boger, D. L. et al. (1999) J. Am. Chem. Soc., 121: 3226-3227). We therefore investigated whether formation of the thioether bridge prior to macrolactamization would result in a different ratio of atropisomers. Removal of the allyl ester from resin-bound linear peptide 3 followed by I$_2$ treatment provided the monocyclic thioether 6 quantitatively (FIG. 7; Scheme 3). Fmoc deprotection and macrolactamization with DPPA yielded a single major product that was ~80% pure by LC/MS. None of the non-natural atropisomer was detected. Side chain deprotection and purification by reversed phase HPLC provided Glu$^7$-phalloidin (2) in 28.5% overall yield based on initial resin loading.

Figure 7:
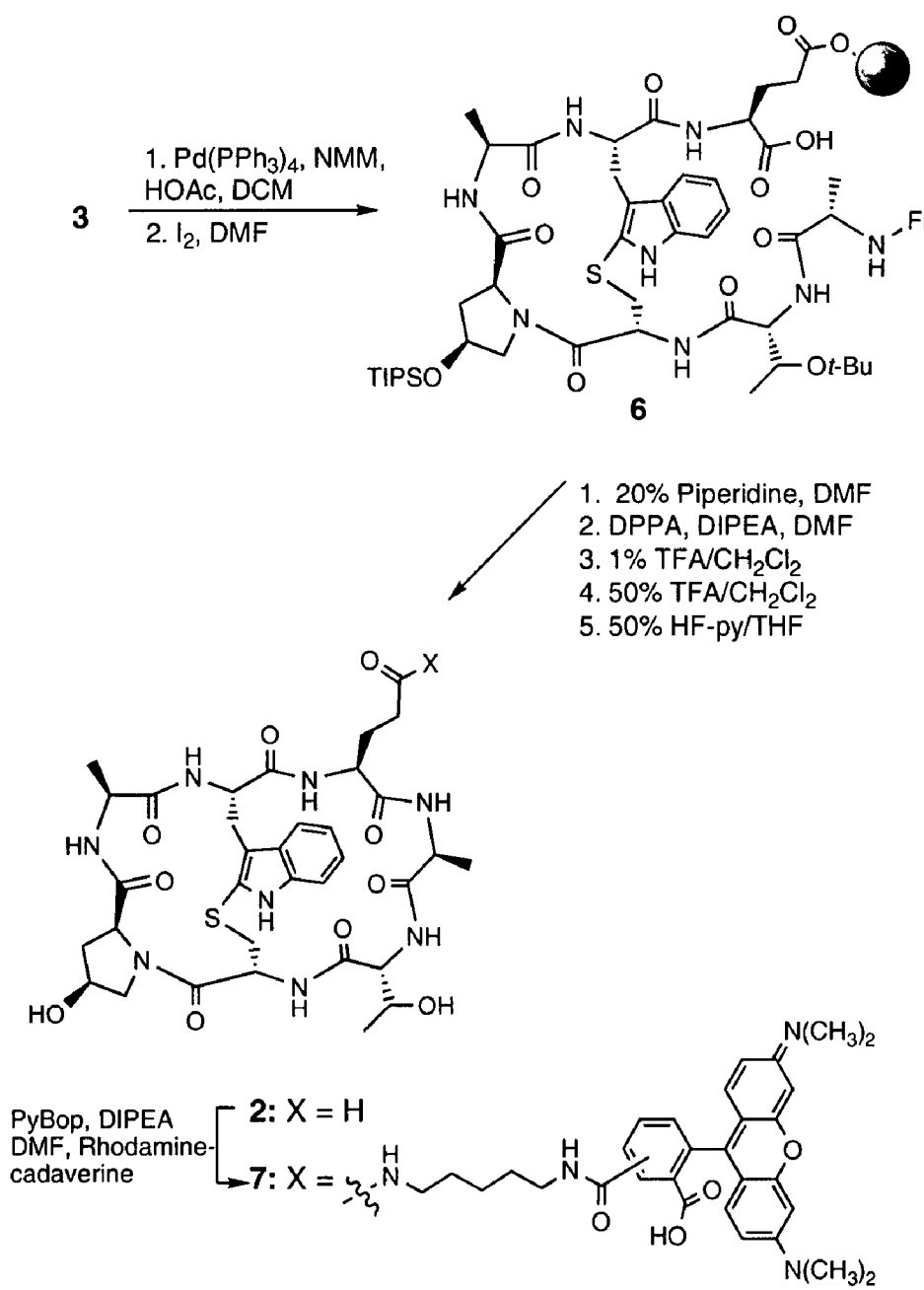
FIG. 7 illustrates a process for conversion of $Glu^7$-phalloidin to a rhodamine derivative (scheme 3).
Figure 9:
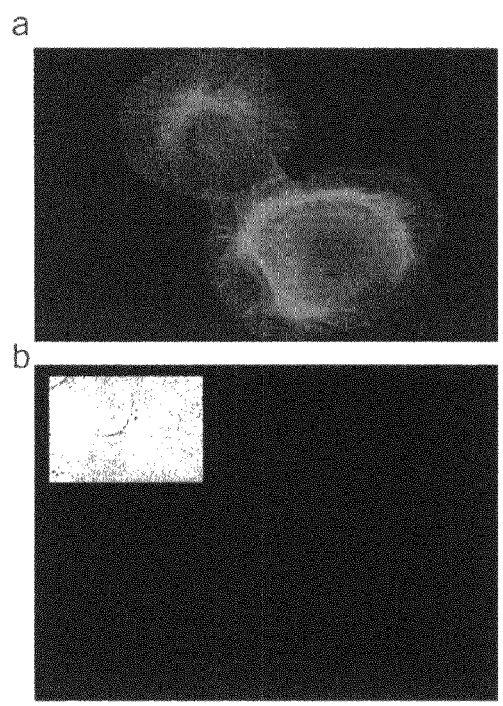
FIG. 9 illustrates photomicrographs showing a) BS-C-1 cells stained with fluorescent phalloidin derivative 7; b) cells pretreated with natural phalloidin 1 prior to addition of 7. Inset image shows phase contrast image of same field.

Conjugation of tetramethylrhodamine-cadaverine to compound 2 was effected using HBTU in dimethylsulfoxide (DMSO), yielding fluorescent adduct 7 (FIG. 7). When cultured mammalian epithelial BS-C-1 cells were fixed and treated with 7 at 20 nM followed by extensive washing, fluorescence microscopy revealed the F-actin staining pattern typical of commercially available phalloidin conjugates (FIG. 9). Actin filament staining was completely abolished when the fixed cells were pretreated with natural phalloidin, demonstrating the specificity of 7 for F-actin (see FIG. 9(b): absence of stain/no image; the inset shows phase contrast image of same field of view showing presence of cells).

Compositions that can be used to label a compound for detecting the presence or absence of the compound when present in a cell or tissue, or when it is bound to a sub-cellular structure or compound, such as to filamentous actin, include, but are not limited to a fluorescent dye, such as, fluorescein, rhodamine, Texas Red, VECTOR Red, ELF™ (Enzyme-Labeled Fluorescence), Cy0, Cy0.5, Cy1, Cy1.5, Cy2, Cy3, Cy3.5, Cy5, Cy7, FluorX, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine, Tryptophan, ATTO labels (Sigma-Aldrich, St. Louis Mo.), RED MEGA labels (Sigma-Aldrich, St. Louis Mo.), and Phycobili proteins, FDNB, FNBT, TNBS, ninhydrin, DABS-Cl, OPA, NDA, fluorescamine, MDF, DNS-Cl, Fmoc-Cl, PITC, radio-active isotopes, and any chemical derivatives thereof, and a non-fluorescent dye, such as, alkaline phosphatase, horseradish peroxidase, glucose oxidase and beta-galactosidase substrate. These labeling compositions can be conjugated to the compound using methods well known to those of skill in the art. Such methods include but are not limited to, fluorescent microscopy, phospho-imaging, scintillation counting, and the like.

Use of Alternative Peptide Substrates

Figure 8:
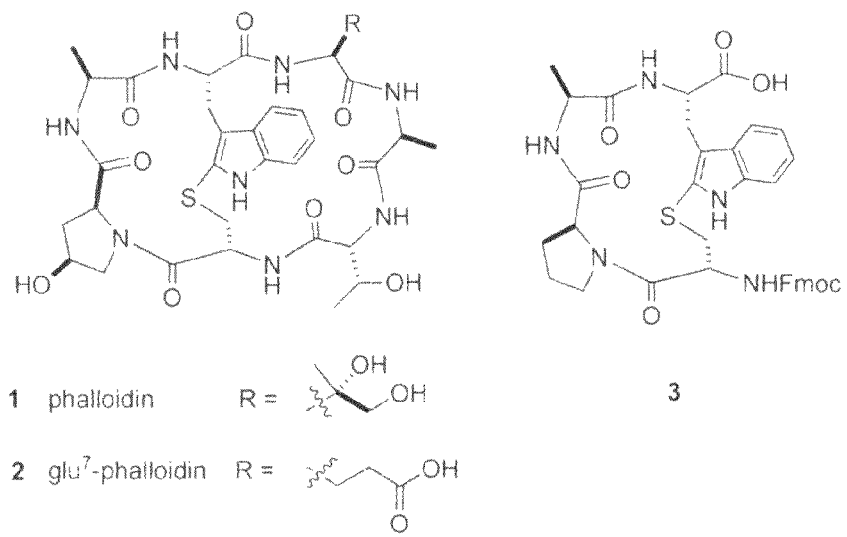
FIG. 8 illustrates a comparison between phalloidin (1), $Glu^7$-phalloidin (2), and a thioether-cyclized compound comprising a model peptide (Cys-LPro-Ala-Trp; SEQ ID NO: 3), the compound derived from the bioactive portion of phalloidin.

Since the major competing reaction to thioether formation is disulfide dimerization, it was reasoned that transfer of the I$_2$-mediated Cys-Trp coupling from solution to the solid phase under low-loading conditions might favor intramolecular cyclization over intermolecular disulfide bond formation. A loading value of ~0.1 mmol/g resin was found to be low enough to minimize disulfide formation for a range of sequences, while still providing enough material to make the reaction practically feasible. A tetrameric model peptide based on the phalloidin-derived sequence Cys(Trt)-Pro-Ala-Trp (SEQ ID NO: 2) reacted with I$_2$ to form the thioether-cyclized product (3) in good overall yield, foreshadowing a successful Trp-Cys coupling in the synthesis of the bicyclic phalloidin scaffold (see FIG. 8).

Expanded structure-activity studies on the phalloidin-actin interaction and evaluation of the generality of this new peptide cyclization strategy using $I_2$-mediated thioether cyclization in the synthesis of cyclic peptides containing the general Cys-Xaa$_n$-Trp motif were performed. Table 1 shows the experimental compound number (column 1), the peptide sequence therein (column 2), and the thioether:disulfide ratio (column 3).

TABLE 1

| SEQ ID NO | compound | peptide | thioether:disulfide ratio |
|---|---|---|---|
| 3 | 3 | Cys-LPro-Ala-Trp | 2.5:1 |
| 4 | 4 | Cys-LPro-Leu-Trp | 3.1:1 |
| 5 | 5 | Cys-LPro-Gly-Trp | 5:1 |
| 6 | 6 | Cys-DPro-Gly-Trp | Exclusive disulfide |
| 7 | 7 | Cys-DPro-Ala-Trp | 0.14:1 |
| 8 | 8 | Cys-DPro-Leu-Trp | 1.26:1 |
| 9 | 9 | Cys-LPro-DAla-Trp | 7.5:1 |
| 10 | 10 | Cys-Gly-LPro-Trp | Exclusive disulfide |
| 11 | 11 | Cys-Leu-LPro-Trp | Exclusive disulfide |
| 12 | 12 | Cys-Gly-DPro-Trp | Exclusive disulfide |
| 13 | 13 | Cys-Leu-DPro-Trp | 1.2:1 |
| 14 | 14 | Cys-cis-Hyp(OTIPS)-Ala-Trp | 8.3:1 |
| 15 | 15 | Cys-cis-Hyp(OTIPS)-Leu-Trp | 8.1:1 |
| 16 | 16 | Cys-trans-Hyp(OH)-Leu-Trp | Exclusive monomer |
| 17 | 17 | Cys-trans-Hyp(OTIPS)-Leu-Trp | 3:1 |
| 18 | 18 | Cys-Gly-Gly-Trp | Exclusive disulfide |
| 19 | 19 | Cys-Ala-Ala-Trp | 1.2:1 |
| 20 | 20 | Cys-Leu-Leu-Trp | 3.8:1 |
| 21 | 21 | Cys-Leu-Leu-Leu-Trp | 0.63:1 |
| 22 | 22 | Cys-Gly-LPro-Leu-Trp | 10:1 |
| 23 | 23 | Cys-LPro-Gly-Leu-Trp | Exclusive monomer |
| 24 | 24 | Cys-Leu-Trp | 0.7:1 |
| 25 | 25 | Cys-Leu-Leu-Leu-Leu-Trp | 1:1 |
| 26 | 26 | Cys-Leu-Leu-Leu-Leu-Leu-Trp | Exclusive monomer |

Note to Table 1:
The thioether monomer and the corresponding disulfide dimer for sequence 4 were fully characterized by 2D $^1$H and $^{13}$C NMR and HRMS. Ratios were determined by integrating the light scattering signal using LC/MS, based on standard curves using known amounts of 4 (monomer and dimer). In all cases, the dimer was easily resolved from the thioether monomer. Dimers for several compounds were verified by on-resin reduction with PBu$_3$ and capping with iodoacetamide. Isolated yield for sequence 4 (monomer + dimer) was 17%. The average purity for all samples by LC/MS was 91% (s.d. 9%).

In particular, cyclization efficiency was measured as a function of sequence length, composition, and $C_\alpha$ stereochemistry. The Fmoc group was retained at the amino terminus to allow for further sequence elongation and entry into more complex lariat-type structures. The major products in nearly all the sequences tested were cyclic thioether and dimeric disulfide, with average post-cleavage purities of 91% (monomer+dimer). Isolated yields on the highly acid labile 2-chlorotrityl resin were lower than expected (17% for sequence 4, monomer+dimer), with the loss occurring at the $I_2$-mediated cyclization step. Yields did not substantially increase, however, when the less labile Rink amide resin was used in place of the 2-chlorotrityl resin (see Schuresko et al. (2007) Org. Lett. in press).

The first sequences that we investigated were tetrapeptides of the sequence H$_2$N-Cys-Pro-Xaa-Trp-OH (SEQ ID NO: 27), where the stereochemistry of the proline and Xaa residues, and the side chain bulk of Xaa, were varied. In phalloidin (FIGS. 1 and 8; 1), the Xaa residue is L-alanine, with a relatively small methyl group. In model peptide 3 (Table 1), L-alanine in the i+2 position yielded a 2.5:1 ratio of thioether monomer to disulfide dimer. As disclosed herein, residues are numbered according to the standard numbering scheme for b-turns; for the tetrapeptides reported in this study, Cys=i and Trp=i+3. When L-alanine was replaced with L-leucine (Table 1, peptide 4), the ratio shifted slightly in favor of the thioether monomer, with an average ratio of 3.1:1 monomer to dimer. When the i+2 residue was replaced with glycine to provide the turn-promoting Pro-Gly sequence found in peptide 5, the ratio increased further to 5:1 in favor of the monomer.

With D-proline in the i+1 position, the resulting series of peptides (peptides 6-8) displayed, on average, much lower cyclization efficiencies than their L-proline-containing diastereomers. The most striking difference was between Cys-LPro-Gly-Trp (5; SEQ ID NO: 5) and Cys-DPro-Gly-Trp (6; SEQ ID NO: 6), in which the L-proline isomer 5 gave a 5:1 ratio of monomer to dimer, while the D-proline isomer 6 gave exclusive disulfide dimer. Molecular modeling studies predicted that 5 takes on a type II β-turn conformation, while 6 adopts a type I' β-turn, consistent with reported observations for known LPro-Gly- and DPro-Gly-containing sequences (see Karle, I. L. and Urry, D. W. (2005) Biopolymers 77: 198-204; Karle, I. et al. (2002) Proc. Natl. Acad. Sci., 99: 5160-5164; Raghothama, S. R. et al. (1998) J. Chem. Soc., Perkin Trans. 2: 137-144; and Haque, T. S. et al. (1996) J. Am. Chem. Soc., 118: 6975-6985). The type II turn predicted for 5 brings the tryptophan indole and cysteine sulfhydryl into close proximity, while the type I' turn in 6 causes the cysteine sulfhydryl to twist away from the indole (FIG. 2), thus disfavoring cyclization.

Further support for the hypothesis that β-turn preference is a primary determinant of thioether formation in the Cys-LPro-Xaa-Trp (SEQ ID NO: 27) series is offered by a comparison of the cyclization efficiencies of 5 (SEQ ID NO: 5; Cys-LPro-Gly-Trp, 5:1), 3 (SEQ ID NO: 3; Cys-LPro-Ala-Trp, 2.5:1), and 9 (SEQ ID NO: 9; Cys-LPro-DAla-Trp, 7.5:1). The i+2 phi and psi dihedrals in type II turns correspond to an allowed region for glycine in the classic Ramachandran plot, and are also part of the "inverted α" region of the Ramachandran plot for D-amino acids (Hutchinson, E. G. and Thornton, J. M. (1994) Prot. Sci., 3: 2207-2216; and Mitchell, J. B. and Smith, J. (2003) Proteins, 50: 563-571). Indeed, the sequence LPro-DXaa is known to preferentially adopt a type II β-turn even in the context of short peptide sequences (Imperiali, B. et al. (1992); J. Am. Chem. Soc., 114: 3182-3188; and Boussard, G. et al. (1974) J. Chim. Phys. 71: 1081-1091). Thus, the favorable effect of D-alanine at the i+2 position is consistent with the formation of a type II β-turn in the transition state of the cyclization reaction.

The effect of D- and L-proline in the i+2 position was explored in peptides 10-13. The two sequences with L-proline at i+2, 10 and 11, both yielded the intermolecular disulfide dimer as the sole product. The two compounds with D-proline in the i+2 position, 12 and 13, gave different results depending on the identity of the i+1 residue. Sequence 12, with glycine in the i+1 position, reacted exclusively to form disulfide dimer, while 13, with leucine at i+1, gave a 1.2:1 ratio of monomer to dimer. L-Proline can occupy the i+2 position of a type VI turn, in which the proline ω dihedral adopts the cis amide geometry (see Muller, G. et al. (1993) Proteins, 15: 235-251). Although the (i)-(i+3) distance (corresponding to the cysteine and tryptophan side chains) is short in the type VI β-turn, this turn is rare in proteins and is primarily found in relatively constrained cyclic peptides (Muller (1993) supra; and Wilmot, C. M. and Thornton, J. M (1988) J. Mol. Biol., 203: 221-232). D-Proline, with a phi angle of +60°, is not found at the i+2 position of any standard turn type. Thus, thioether formation can occur even in the absence of classic turn-promoting sequences and may yield interesting scaffolds in compounds based on the Cys-Xaa-DPro-Trp (SEQ ID NO: 28) motif.

Phalloidin contains an unusual cis-4-hydroxyproline (cis-Hyp) residue, which was protected as a triisopropylsilyl (TIPS) ether in the synthesis of $Glu^7$-phalloidin as disclosed herein. The presence of the TIPS-protected hydroxyl group in the cis configuration (14 and 15) led to a significant improvement in cyclization efficiency compared with the corresponding non-hydroxylated sequences (3 and 4). Peptide 16 (Cys-trans-Hyp(OH)-Leu-Trp; SEQ ID NO: 16), in which the trans hydroxyl group was unprotected, showed exclusive formation of cyclic thioether, compared to 3:1 (monomer:dimer) for 17 and 8.1:1 for 15. Of note, these distal modifications to the proline ring may have a significant long-range effect on the outcome of the macrocyclization reaction; however, we were not yet able to account for these observations using the same modeling approach applied to 5 and 6 above.

Exploring cyclization efficiency in peptides without proline (18-21), the steric bulk of the i+1 and i+2 residues had a significant impact on cyclization. Sequence 20 (Cys-Leu-Leu-Trp; SEQ ID NO: 20) gave cyclomonomer in a 3.8:1 ratio, while 19 (Cys-Ala-Ala-Trp; SEQ ID NO: 19) dropped to 1.2:1 and 18 (Cys-Gly-Gly-Trp; SEQ ID NO: 18) gave the disulfide dimer product exclusively. In these cases, entropy may be the major factor, in which the bulkier side chains limit the degrees of freedom in the linear precursor such that cyclization outweighs disulfide formation even in the absence of a well-defined turn structure.

Insertion of an additional leucine residue (21, Cys-Leu-Leu-Leu-Trp; SEQ ID NO: 21) yielded a significant decrease in cyclization efficiency compared to tetrapeptide 20 (Cys-Leu-Leu-Trp: SEQ ID NO: 20). However, placement of L-proline within the pentamer sequences caused a dramatic increase in cyclization efficiency. Insertion of a glycine between cysteine and L-proline resulted in a significant increase in monomer formation, from 3.1:1 in 4 to 10:1 in 22. This could be due to the ~10-fold higher preference for glycine over cysteine in the i position of type II turns (Hutchinson, E. G. and Thornton, J. M. (1994) supra), or it could reflect a general length dependence in the cyclization reaction. Support for the latter is provided by a comparison between 23 and 5, in which insertion of a leucine residue after the turn promoting LPro-Gly sequence dramatically improved the cyclization efficiency (from 5:1 in 5 to >100:1 in 23). Interestingly, removal of a leucine residue to generate tripeptide 24 lowered the cyclization efficiency relative to tetrapeptide 20, while longer sequences such as 26 and 27 provided highly efficient access to cyclomonomer.

Thus, an $I_2$-mediated Cys-Trp thioether formation into a mild solid phase cyclization strategy has been developed. Investigations into the effect of peptide sequence, stereochemistry, and length on the reaction have revealed that although turn-promoting sequences significantly enhance cyclization, the reaction is also relatively efficient even among sequences with no known β-turn propensity. The chemistry is general and mild enough to be applied, in principle, toward the synthesis of cyclic peptide libraries based on the Cys-Trp thioether linkage.

In summary, we have developed a simple synthesis of $Glu^7$-phalloidin and its derivatives, including a fluorescent bioactive probe that is as effective as natural phalloidin conjugates in staining F-actin in fixed cells. This route will generate sufficient amounts of fluorescently labeled phalloidin to perform high-throughput image-based screens for compounds that affect actin morphology, and will allow us to make extensive modifications to the phalloidin scaffold for future structure-activity studies.

Binding Assay for Cyclomonomer

Saturability in the binding of a cyclomonomer demonstrates the existence of a limited number of binding sites and is the hallmark of specificity. Saturability is demonstrated if binding of a labeled cyclomonomer can be serially reduced by increasing quantities of the native, unlabeled cyclomonomer. Such data also demonstrate that the labeled cyclomonomer remains sufficiently bio-relevant that its distribution is a valid report of the distribution of the unlabeled molecule. Biological processes are time- and temperature-dependent, for example, crossing a barrier such as the plasma membrane. In particular, at low temperatures (cells held over ice) endosomal traffic would be halted, but permeation through pores or channels could continue, albeit more slowly.

The substrate used for binding thereto is preferably filamentous actin (F-actin), but can also be a synthetic peptide having similar chemical and/or biochemical properties as F-actin, it can be globular actin (G-actin), or it can be any derivatives thereof.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

While the above is a complete description of the preferred embodiments of the invention, various alternatives, modifications, and equivalents may be used. Therefore, the above description should not be taken as limiting the scope of the invention which is defined only by the claims and any amendments thereto.

We claim:

1. A method for synthesizing a cyclomonomer having actin binding activity, the method comprising the steps of (i) α-protecting the N-terminus of glutamate using base-labile 9-fluorenylmethyloxycarbonyl (Fmoc), (ii) protecting the C-terminal of the Fmoc-protected glutamate using allyl ester to create a modified glutamate, (iii) linking the side chain of the modified glutamate to 2-chlorotrityl polystyrene resin, (iv) linking the N-terminus of the modified glutamate to tryptophan using standard Fmoc chemistry thereby creating a dipeptide, (v) elongating the dipeptide with N-α-protected alanine using standard Fmoc chemistry thereby creating a tripeptide, (vi) elongating the tripeptide with N-α-protected cis-4-hydroxy-proline using standard Fmoc chemistry thereby creating a tetrapeptide, (vii) elongating the tetrapeptide with N-α-protected, S-trityl protected cysteine using standard Fmoc chemistry thereby creating a pentapeptide, (viii) elongating the pentapeptide with N-α-protected D-threonine using standard Fmoc chemistry thereby creating a hexapeptide, (ix) elongating the hexapeptide with N-α-protected alanine using standard Fmoc chemistry thereby creating a heptapeptide, (x) removing the N-terminal Fmoc and the C-terminal allyl ester, (xi) deprotecting the heptapeptide using tetrakis(triphenylphosphine palladium ($Pd(PPh_3)_4$), N-methylmorpholine (NMM), acetic acid, dichloromethane (DCM), 20% piperidine, and dimethylfluoride (DMF) thereby creating a modified heptapeptide, (xii) cyclizing the modified heptapeptide using diphenylphosphorylazide (DPPA), N,N-diisopropylethylamine (DIPEA), and DMF thereby creating a cyclomonomer, (xiii) treating the cyclomonomer with $I_2$ in DMF thereby creating a thioether bond between the cysteine residue (Cys3) and the tryptophan residue (Trp6), wherein S-3→6 represents the thioether bond between Cys3 and Trp6, and resulting in a thioether cyclomonomer, and (xiv) cleaving the thioether cyclomonomer from the resin using 1% TFA in $CH_2Cl_2$, the steps resulting in the synthesis of bicyclo(Ala1-D-Thr2-Cys3-cis-3-hydroxy-Pro-4-Ala5-2-mercapto-Trp6-Glu7) (S 36) having actin binding activity.

2. The method of claim 1 wherein the method further comprises the step of elongating the tripeptide using side chain-protected cis-4-hydroxy-proline.

3. The method of claim 1 wherein the method further comprises the step of elongating the pentapeptide using side chain-protected D-threonine.

4. The method of claim 1 wherein the method further comprises the step of treating the thioether cyclomonomer using 50% TFA in $CH_2Cl_2$.

5. The method of claim 1 wherein the method further comprises the step of treating the thioether cyclomonomer using 50% HF in THF.

* * * * *

SEQUENCE LISTING

```
<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: competitor peptide; part of thioester sequence
      of Amanita phalloides phalloidin; exemplary sequence

<400> SEQUENCE: 1

Cys Pro Ala Trp
1
```

```
<210> SEQ ID NO 2
<211> LENGTH: 4
<212> TYPE: PRT
<213> ORGANISM: Artificial Sequence
<220> FEATURE:
<223> OTHER INFORMATION: phalloidin-derived sequence; part of thioester
      sequence of Amanita phalloides phalloidin; exemplary sequence
<220> FEATURE:
<221> NAME/KEY: misc_feature
<222> LOCATION: (1)
<223> OTHER INFORMATION: Trt-modified Cys

<400> SEQUENCE: 2

Cys Pro Ala Trp
1

<210> SEQ ID NO 3
<211> LENGTH: 4
<212> TYPE: PRT
<213> ORGANISM: Artificial Sequence
<220> FEATURE:
<223> OTHER INFORMATION: Model peptide 3; part of thioester sequence of
      Amanita phalloides phalloidin; exemplary sequence
<220> FEATURE:
<221> NAME/KEY: misc_feature
<222> LOCATION: (2)
<223> OTHER INFORMATION: L-isomer Proline

<400> SEQUENCE: 3

Cys Pro Ala Trp
1

<210> SEQ ID NO 4
<211> LENGTH: 4
<212> TYPE: PRT
<213> ORGANISM: Artificial Sequence
<220> FEATURE:
<223> OTHER INFORMATION: Model peptide 4; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: L-isomer Proline

<400> SEQUENCE: 4

Cys Pro Leu Trp
1

<210> SEQ ID NO 5
<211> LENGTH: 4
<212> TYPE: PRT
<213> ORGANISM: Artificial Sequence
<220> FEATURE:
<223> OTHER INFORMATION: Model peptide 5; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: L-isomer Proline

<400> SEQUENCE: 5

Cys Pro Gly Trp
1

<210> SEQ ID NO 6
<211> LENGTH: 4
<212> TYPE: PRT
<213> ORGANISM: Artificial Sequence
```

-continued

```
<220> FEATURE:
<223> OTHER INFORMATION: Model peptide 6; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: D-isomer Proline

<400> SEQUENCE: 6

Cys Pro Gly Trp
1

<210> SEQ ID NO 7
<211> LENGTH: 4
<212> TYPE: PRT
<213> ORGANISM: Artificial Sequence
<220> FEATURE:
<223> OTHER INFORMATION: Model peptide 7; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: D-isomer Proline

<400> SEQUENCE: 7

Cys Pro Ala Trp
1

<210> SEQ ID NO 8
<211> LENGTH: 4
<212> TYPE: PRT
<213> ORGANISM: Artificial Sequence
<220> FEATURE:
<223> OTHER INFORMATION: Model peptide 8; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: D-isomer Proline

<400> SEQUENCE: 8

Cys Pro Leu Trp
1

<210> SEQ ID NO 9
<211> LENGTH: 4
<212> TYPE: PRT
<213> ORGANISM: Artificial Sequence
<220> FEATURE:
<223> OTHER INFORMATION: Model peptide 9; part of thioester sequence of
      Amanita phalloides phalloidin; exemplary sequence; substituted
      variant
<220> FEATURE:
<221> NAME/KEY: misc_feature
<222> LOCATION: (2), (3)
<223> OTHER INFORMATION: L-isomer Proline; D-isomer Alanine

<400> SEQUENCE: 9

Cys Pro Ala Trp
1

<210> SEQ ID NO 10
<211> LENGTH: 4
<212> TYPE: PRT
<213> ORGANISM: Artificial Sequence
<220> FEATURE:
<223> OTHER INFORMATION: Model peptide 10; part of thioester sequence of
      Amanita phalloides phalloidin; exemplary sequence; substituted
      variant
```

```
<220> FEATURE:
<221> NAME/KEY: misc_feature
<222> LOCATION: (3)
<223> OTHER INFORMATION: L-isomer Proline

<400> SEQUENCE: 10

Cys Gly Pro Trp
1

<210> SEQ ID NO 11
<211> LENGTH: 4
<212> TYPE: PRT
<213> ORGANISM: Artificial Sequence
<220> FEATURE:
<223> OTHER INFORMATION: Model peptide 11; part of thioester sequence of
      Amanita phalloides phalloidin; exemplary sequence; substituted
      variant
<220> FEATURE:
<221> NAME/KEY: misc_feature
<222> LOCATION: (3)
<223> OTHER INFORMATION: L-isomer Proline

<400> SEQUENCE: 11

Cys Leu Pro Trp
1

<210> SEQ ID NO 12
<211> LENGTH: 4
<212> TYPE: PRT
<213> ORGANISM: Artificial Sequence
<220> FEATURE:
<223> OTHER INFORMATION: Model peptide 12; part of thioester sequence of
      Amanita phalloides phalloidin; exemplary sequence; substituted
      variant
<220> FEATURE:
<221> NAME/KEY: misc_feature
<222> LOCATION: (3)
<223> OTHER INFORMATION: D-isomer Proline

<400> SEQUENCE: 12

Cys Gly Pro Trp
1

<210> SEQ ID NO 13
<211> LENGTH: 4
<212> TYPE: PRT
<213> ORGANISM: Artificial Sequence
<220> FEATURE:
<223> OTHER INFORMATION: Model peptide 13; part of thioester sequence of
      Amanita phalloides phalloidin; exemplary sequence; substituted
      variant
<220> FEATURE:
<221> NAME/KEY: misc_feature
<222> LOCATION: (3)
<223> OTHER INFORMATION: D-isomer Proline

<400> SEQUENCE: 13

Cys Leu Pro Trp
1

<210> SEQ ID NO 14
<211> LENGTH: 4
<212> TYPE: PRT
<213> ORGANISM: Artificial Sequence
<220> FEATURE:
<223> OTHER INFORMATION: Model peptide 14; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: Xaa represents TIPS-protected Hydroxyproline;
```

```
                                cis-Hydroxyproline

<400> SEQUENCE: 14

Cys Xaa Ala Trp
1

<210> SEQ ID NO 15
<211> LENGTH: 4
<212> TYPE: PRT
<213> ORGANISM: Artificial Sequence
<220> FEATURE:
<223> OTHER INFORMATION: Model peptide 15; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: Xaa represents TIPS-protected Hydroxyproline;
      cis-Hydroxyproline

<400> SEQUENCE: 15

Cys Xaa Leu Trp
1

<210> SEQ ID NO 16
<211> LENGTH: 4
<212> TYPE: PRT
<213> ORGANISM: Artificial Sequence
<220> FEATURE:
<223> OTHER INFORMATION: Model peptide 16; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: Xaa represents Hydroxyproline;
      trans-Hydroxyproline

<400> SEQUENCE: 16

Cys Xaa Leu Trp
1

<210> SEQ ID NO 17
<211> LENGTH: 4
<212> TYPE: PRT
<213> ORGANISM: Artificial Sequence
<220> FEATURE:
<223> OTHER INFORMATION: Model peptide 17; part of thioester sequence of
      Amanita phalloides phalloidin; exemplary sequence; substituted
      variant
<220> FEATURE:
<221> NAME/KEY: misc_feature
<222> LOCATION: (2)
<223> OTHER INFORMATION: Xaa represents TIPS-protected Hydroxyproline;
      trans-Hydroxyproline

<400> SEQUENCE: 17

Cys Xaa Leu Trp
1

<210> SEQ ID NO 18
<211> LENGTH: 4
<212> TYPE: PRT
<213> ORGANISM: Artificial Sequence
<220> FEATURE:
<223> OTHER INFORMATION: Model peptide 18; part of thioester sequence of
      Amanita phalloides phalloidin; exemplary sequence; substituted
      variant

<400> SEQUENCE: 18

Cys Gly Gly Trp
```

1

<210> SEQ ID NO 19
<211> LENGTH: 4
<212> TYPE: PRT
<213> ORGANISM: Artificial Sequence
<220> FEATURE:
<223> OTHER INFORMATION: Model peptide 19; part of thioester sequence of
Amanita phalloides phalloidin; exemplary sequence; substituted
variant

<400> SEQUENCE: 19

Cys Ala Ala Trp
1

<210> SEQ ID NO 20
<211> LENGTH: 4
<212> TYPE: PRT
<213> ORGANISM: Artificial Sequence
<220> FEATURE:
<223> OTHER INFORMATION: Model peptide 20; part of thioester sequence of
Amanita phalloides phalloidin; exemplary sequence; substituted
variant

<400> SEQUENCE: 20

Cys Leu Leu Trp
1

<210> SEQ ID NO 21
<211> LENGTH: 5
<212> TYPE: PRT
<213> ORGANISM: Artificial Sequence
<220> FEATURE:
<223> OTHER INFORMATION: Model peptide 21; part of thioester sequence of
Amanita phalloides phalloidin; exemplary sequence; substituted
variant

<400> SEQUENCE: 21

Cys Leu Leu Leu Trp
1 5

<210> SEQ ID NO 22
<211> LENGTH: 5
<212> TYPE: PRT
<213> ORGANISM: Artificial Sequence
<220> FEATURE:
<223> OTHER INFORMATION: Model peptide 22; part of thioester sequence of
Amanita phalloides phalloidin; exemplary sequence; substituted
variant
<220> FEATURE:
<221> NAME/KEY: misc_feature
<222> LOCATION: (3)
<223> OTHER INFORMATION: L-isomer Proline

<400> SEQUENCE: 22

Cys Gly Pro Leu Trp
1 5

<210> SEQ ID NO 23
<211> LENGTH: 5
<212> TYPE: PRT
<213> ORGANISM: Artificial Sequence
<220> FEATURE:
<223> OTHER INFORMATION: Model peptide 23; part of thioester sequence of
Amanita phalloides phalloidin; exemplary sequence; substituted
variant
<220> FEATURE:
<221> NAME/KEY: misc_feature
<222> LOCATION: (2)
<223> OTHER INFORMATION: L-isomer Proline

```
<400> SEQUENCE: 23

Cys Pro Gly Leu Trp
1               5

<210> SEQ ID NO 24
<211> LENGTH: 3
<212> TYPE: PRT
<213> ORGANISM: Artificial Sequence
<220> FEATURE:
<223> OTHER INFORMATION: Model peptide 24; part of thioester sequence of
      Amanita phalloides phalloidin; exemplary sequence; substituted
      variant

<400> SEQUENCE: 24

Cys Leu Trp
1

<210> SEQ ID NO 25
<211> LENGTH: 6
<212> TYPE: PRT
<213> ORGANISM: Artificial Sequence
<220> FEATURE:
<223> OTHER INFORMATION: Model peptide 25; part of thioester sequence of
      Amanita phalloides phalloidin; exemplary sequence; substituted
      variant

<400> SEQUENCE: 25

Cys Leu Leu Leu Leu Trp
1               5

<210> SEQ ID NO 26
<211> LENGTH: 7
<212> TYPE: PRT
<213> ORGANISM: Artificial Sequence
<220> FEATURE:
<223> OTHER INFORMATION: Model peptide 26; part of thioester sequence of
      Amanita phalloides phalloidin; exemplary sequence; substituted
      variant

<400> SEQUENCE: 26

Cys Leu Leu Leu Leu Leu Trp
1               5

<210> SEQ ID NO 27
<211> LENGTH: 4
<212> TYPE: PRT
<213> ORGANISM: Artificial Sequence
<220> FEATURE:
<223> OTHER INFORMATION: Model tetrapeptides; part of thioester sequence
      of Amanita phalloides phalloidin; exemplary sequence; substituted
      variants
<220> FEATURE:
<221> NAME/KEY: Variant
<222> LOCATION: (3)
<223> OTHER INFORMATION: Ala, Cys, Asp, Glu, Phe, Gly, His, Ile, Lys,
      Leu, Met, Asn, Pro, Gln, Arg, Ser, Thr, Val, Trp, Tyr

<400> SEQUENCE: 27

Cys Pro Xaa Trp
1

<210> SEQ ID NO 28
<211> LENGTH: 4
<212> TYPE: PRT
<213> ORGANISM: Artificial Sequence
<220> FEATURE:
<223> OTHER INFORMATION: Model tetrapeptides; part of thioester sequence
      of Amanita phalloides phalloidin; exemplary sequence; substituted
      variants
<220> FEATURE:
```

-continued

```
<221> NAME/KEY: Variant
<222> LOCATION: (2)
<223> OTHER INFORMATION: Ala, Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: misc_feature
<222> LOCATION: (3)
<223> OTHER INFORMATION: D-isomer Proline

<400> SEQUENCE: 28

Cys Xaa Pro Trp
1
```